United States Patent [19]

Ishizumi et al.

[11] Patent Number: 4,843,078
[45] Date of Patent: Jun. 27, 1989

[54] SUCCINIMIDE DERIVATIVES, AND THEIR PRODUCTION AND USE

[75] Inventors: Kikuo Ishizumi, Toyonaka; Fujio Antoku, Takarazuka; Isamu Maruyama, Kawanishi; Atsuyuki Kojima, Takarazuka, all of Japan

[73] Assignee: Sumitono Pharmaceutical Company, Limited, Osaka, Japan

[21] Appl. No.: 182,085

[22] Filed: Apr. 15, 1988

Related U.S. Application Data

[63] Continuation-in-part of Ser. No. 852,202, Apr. 15, 1986, abandoned.

[30] Foreign Application Priority Data

Apr. 17, 1985 [JP] Japan .................................. 60-83297

[51] Int. Cl.$^4$ .................. A61K 31/505; C07D 403/14; C07D 401/14
[52] U.S. Cl. ..................................... 514/253; 544/295; 544/364
[58] Field of Search ................. 544/295, 364; 514/253

[56] References Cited

U.S. PATENT DOCUMENTS

| 2,672,460 | 3/1954 | Conroy | 544/364 |
| 4,507,303 | 3/1985 | Ishizumi et al. | 544/295 |
| 4,524,206 | 6/1985 | New et al. | 544/250 |
| 4,543,355 | 9/1985 | Ishizumi et al. | 544/295 |
| 4,562,255 | 12/1985 | Freed et al. | 544/295 |
| 4,567,180 | 1/1986 | Hirose et al. | 544/295 |
| 4,598,078 | 7/1986 | Ishizumi et al. | 544/295 |

FOREIGN PATENT DOCUMENTS 0109562 5/1984 European Pat. Off. .
0111226 6/1984 European Pat. Off. .
0082402 4/1986 European Pat. Off. .
2506771 12/1982 France .
2146333 4/1985 United Kingdom .

OTHER PUBLICATIONS

Yevich et al., "Journal of Medicinal Chemistry", vol. 26, pp. 194–203 (1983).

Primary Examiner—Richard L. Raymond
Assistant Examiner—James H. Turnipseed
Attorney, Agent, or Firm—Birch, Stewart, Kolasch & Birch

[57] ABSTRACT

A succinimide derivative of the formula:

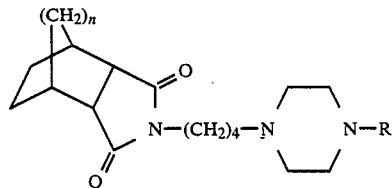

wherein R is a pyridyl or pyrimidinyl group substituted with at least one member selected from the group consisting of halogen, lower alkyl, lower alkoxy, cyano, benzyloxy, hydroxyl and amino, and n is an integer of 1 or 2, or a pharmaceutically acceptable acid addition salt thereof. The succinimide derivatives are useful as an anti-anxiety drugs.

21 Claims, No Drawings

SUCCINIMIDE DERIVATIVES, AND THEIR PRODUCTION AND USE

This is a continuation-in-part application of our application Ser. No. 852,202 filed Apr. 15, 1986, and now abandoned.

The present invention relates to novel succinimide derivatives, and their production and use. More particularly, the present invention relates to novel succinimide derivatives having a piperazinylbutyl group at the N-position or their acid addition salts, their preparation process, and their anxiolytic use.

The succinimide derivatives of this invention are represented by the formula:

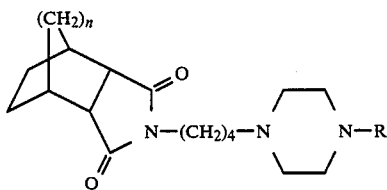

wherein R is a pyridyl or pyrimidinyl group substituted with at least one member selected from the group consisting of halogen, lower alkyl, lower alkoxy, cyano, benzyloxy, hydroxyl and amino, and n is an integer of 1 or 2.

In the above definitions, the term "halogen" includes fluorine, chlorine, bromine and iodine. The term "lower alkyl" includes a straight or branched alkyl group having 1 to 4 carbon atoms such as methyl, ethyl, n-propyl, isopropyl, n-butyl or isobutyl. The term "lower alkoxy" includes a straight or branched alkoxy group having 1 to 4 carbon atoms such as methoxy, ethoxy, n-propoxy, isopropoxy, n-butoxy or isobutoxy.

Among the succinimide derivatives (I), preferred are those wherein R is a pyridyl group substituted with at least one substituent selected from the group consisting of halogen, methoxy and cyano or a pyrimidinyl group substituted with at least one substituent selected from the group consisting of halogen, methyl, methoxy, benzyloxy, hydroxyl and amino.

The succinimide derivatives (I) can form salts with acids. Suitable pharmaceutically acceptable acid addition salts are those with inorganic acids such as hydrochloric acid, hydrobromic acid, sulfuric acid and phosphoric acid or organic acids such as acetic acid, propionic acid, butyric acid, oxalic acid, succinic acid, tartaric acid, citric acid, maleic acid and fumaric acid.

The succinimide derivatives (I) of the present invention can be prepared by the process as shown in the following scheme:

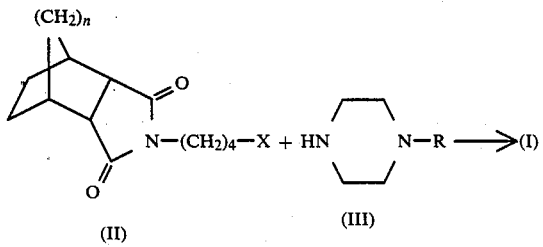

wherein R and n are each as defined above and X is a halogen atom (e.g. chlorine, bromine, iodine).

Namely, the succinimide derivative (I) is obtainable by reacting the compound (II) with the compound (III), preferably in the presence of an acid binding agent in an inert solvent (e.g. benzene, toluene, xylene, N,N-dimethylformamide, acetonitrile, n-butanol, acetone) at room temperature or at an elevated temperature. The acid binding agent may be chosen from alkali metal or alkaline earth metal carbonates, bicarbonates and hydrides (e.g. potassium carbonate, sodium bicarbonate, sodium hydride), organic tertiary amines (e.g. triethylamine, pyridine), etc.

Among the succinimide derivatives (I), the one of the following formula:

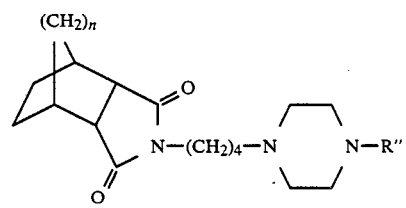

wherein R" is a pyridyl or pyrimidinyl group substituted with hydroxy and n is as defined above, may be produced by subjecting a compound of the formula:

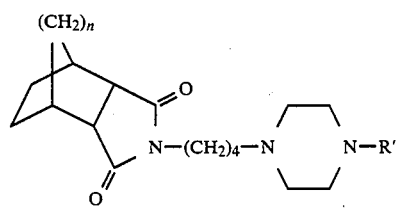

wherein R' is a pyridyl or pyrimidinyl group substituted with benzyloxy and n is as defined above, to a reduction reaction.

The above reduction reaction is usually carried out by hydrogenating the compound (I-a) in the presence of a catalyst in an inert solvent. As the catalyst, there may be employed any one conventionally used for hydrogenation, and specific examples include platinum catalysts (e.g. platinum black, platinum dioxide, platinum colloid), palladium catalysts (e.g. palladium black, palladium on carbon, palladium colloid), rhodium catalysts, nickel catalysts (e.g. Raney nickel, nickel oxide), etc. Examples of the solvent are lower alkanols (e.g. methanol, ethanol, isopropanol), water, acetic acid, ethyl acetate, tetrahydrofuran, dioxane, etc. The hydrogenation may be effected under atmospheric pressure or at an elevated pressure, and at room temperature or at an elevated temperature.

The starting compounds (II) and (III) used in the above process are per se known or can be produced from the known compounds by a per se conventional procedure. For instance, the compound (II), i.e. the N-halobutylsuccinimide compound, may be prepared from the corresponding N-unsubstituted succinimide compound according to a procedure as described in Japanese Patent Publication (unexamined) No. 87262/1985 and EP-A-117569. Likewise, the compound (III), i.e. the N-substituted piperazine, may be produced from the corresponding N-unsubstituted piperazine according to a procedure described in those publications.

As anti-anxiety drugs, benzodiazepine compounds such as diazepam have mostly been used. These benzodiazepine compounds have, however, a strong central nervous system depressing activity. For instance, they produce a potent potentiation of hexobarbital anesthesia, which is an index of sleepiness, and in fact, some benzodiazepine compounds are used as sleep inducing drugs. Such depressing activity of the central nervous system is an unfavorable side effect for their use as anti-anxiety drugs.

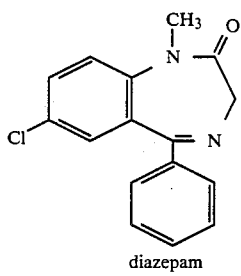

diazepam

Spiroimide compounds (e.g. buspirone) and succinimide compounds (e.g. SM-3997) as recently developed have considerably alleviated depressing activity of the central nervous system such as potentiation of hexobarbital anesthesia in comparison with benzodiazepine compounds. Therefore, they are useful as selective anti-anxiety drugs.

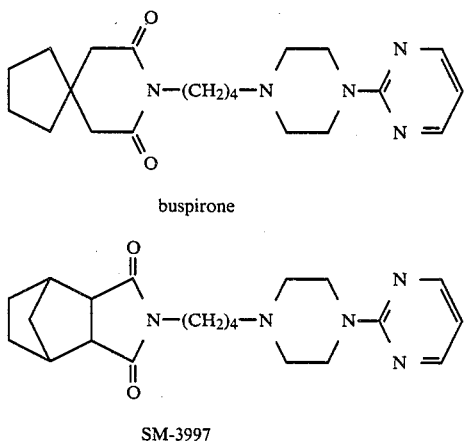

buspirone

SM-3997

The succinimide derivatives (I) of the invention have been found to exert anxiolytic activity while decreasing the depressing activity of the central nervous system for a prolonged period of time. Namely, they have an anti-anxiety effect with a weak sleepiness inducing effect, and therefore they can be used for patients suffering from anxiety and also for patients suffering from slight sleeplessness. These properties of the succinimide derivatives (I) are evidenced by the pharmacological test results as set forth below.

Results of pharmacological test:

(1) Anti-anxiety activity

The anti-anxiety activity of the succinimide derivatives (I) was proved by the anti-conflict test, which was carried out according to the method as described in Vogel et al.: Psychopharmacologia, 21, 1 (1971) with some modifications.

SD strain male rats (bodyweight, 200 to 240g) were abstained from water 24 hours before the test and charged in a measuring device which was designed so as to measure the frequency of water drinking, i.e. the number of licks (6 licks corresponding to water drinking for 1 second), by rats in 3 minutes from the start of drinking and to count the frequency of sustaining electric shocks. Initially, no electric shocks were charged at all. Rats showing more than 300 licks were further abstained from water for 24 hours. Thereafter, the frequency of water drinking by those rats was counted while applying one electric shock (70 V, 0.35 mA) per 20 licks. Rats, of which the frequency of water drinking was suppressed to 260 licks by the electric shocks, were regarded as being in a conflict state and subjected to the test.

The rats were divided into several groups (8 to 10 rats per one group), and the test compounds were intraperitoneally administered to them. One hour after administration, rats were again charged in the measuring device, and the frequency of electric shocks accompanied by drinking water was counted while applying the electric shocks. As the control, there was used diazepam, which is a known anti-anxiety drug. The results are shown in Table 1.

TABLE 1

| Compound | Dose (mg/kg) (i.p.) |
|---|---|
| N—[4-{4-(5-Fluoro-2-pyrimidinyl-1-piperazinyl}butyl]bicyclo[2.2.1]heptane-2,3-di-exo-carboximide (Compound No. 1) | 4 |
| N—[4-{4-(3-Chloro-2-pyridyl-1-piperazinyl}butyl]bicyclo[2.2.1]heptane-2,3-di-exo-carboximide (Compound No. 9) | 2 |
| Diazepam | 2 |

It is apparent from the above test results that anti-conflict activity of the succinimide derivatives (I) is nearly equal to that of diazepam.

(2) Potentiating activity of hexobarbital anesthesia

The test was carried out according to the method as described by Ueki et al: Folia Farmacol. Japon, 77, 483–509 (1981)" with some modifications.

The test compound was orally administred to dd strain of male mice (bodyweight, 23 to 27 g), and after one hour, hexobarbital (100 mg/kg) was intraperitoneally administered to the mice. The duration of anesthesia, as measured by the loss of righting reflex, was recorded for each mouse. When the anesthetized time by hexobarbital extended more than 2 times over the average time in the control group, anesthesia potentiation was regarded as positive (+).

The results are shown in Table 2.

TABLE 2

| Compound | Dose (mg/kg) (p.o.) | Judgement |
|---|---|---|
| Diazepam | 1 | + |
| Compound No. 1 | 100 | + |
| Compound No. 9 | 100 | + |
| SM-3997 | 100 | negative |
| Buspirone | 100 | negative |

According to the anti-climbing test in mice [Protais et al.: Psychopharmacology, 50, 1–6 (1976)], some of the succinimide derivatives (I) including Compound Nos. 1 and 9 have proved to exhibit significant anti-psychotic activity. Accordingly, they may be used for the treatment of psychosis.

In general, the succinimide derivatives (I) exhibit central activity with weak peripheral side action. Their central activity is thus selective.

For therapeutic use, the succinimide derivatives (I) or their acid addition salts may be formulated into conventional pharmaceutical preparation forms suitable for oral or parenteral administration. Examples of such pharmaceutical preparation forms are tablets, capsules, solutions, etc. In the formulation, they are usually combined with suitable carriers or diluents such as fillers, binders or stabilizers.

The dosage of the succinimide derivatives (I) may vary and it also depends upon the degree of symptoms, the age and bodyweight of a patient, the route of administration, etc. In the case of oral administration, the compound can be, in general, administered to an adult in a daily amount of from about 0.2 to 1500 milligrams, preferably from about 1 to 500 milligrams, at once or in intervals.

The present invention will be further illustrated in detail by means of the following Reference Examples and Examples, which are not, however, intended to limit the scope of the invention.

REFERENCE EXAMPLE 1

A mixture of bicyclo[2.2.1]heptane-2,3-di-exo-carboximide (50 g), tetramethylene bromide (327 g), potassium carbonate (50 g) and acetone (500 ml) was heated under reflux for 5 hours. The mixture was cooled to room temperature, and insoluble materials were removed by filtration. The filtrate was concentrated by distillation under reduced pressure to give N-(4-bromobutyl)bicyclo[2.2.1]heptane-2,3-di-exo-carboximide (71.4 g) as an oil. Yield, 78.6 %. B.P., 173°–180° C./0.04 mmHg. IR $\nu_{max}^{film}$ (cm$^{-1}$): 1765, 1700, 1430, 1395.

In the same manner as in Reference Example 1, there were obtained the following compounds:

N-(4-Bromobutyl)bicyclo[2.2.1]heptane-2,3-di-endo-carboximide. IR $\nu_{max}^{film}$ (cm$^{-1}$): 1765, 1700;

N-(4-Bromobutyl)bicyclo[2.2.2]octane-2,3-di-carboximide. IR $\nu_{max}^{film}$ (cm$^{-1}$): 1760, 1690.

REFERENCE EXAMPLE 2

A solution of 2,3-chloropyridine (13.1 g) and anhydrous piperazine (37.9 g) in n-butanol (350 ml) was heated under reflux for 16 hours. The solvent was removed by evaporation under reduced pressure, and the residue was diluted with aqueous sodium hydroxide solution and extracted with dichloromethane. From the extract, the solvent was removed by distillation under reduced pressure to give 1-(3-chloro-2-pyridyl)piperazine (15.7 g) as an oil. IR $\nu_{max}^{film}$ (cm$^{-1}$): 3280, 1575. M.P., 142°–144° C. (hydrochloride).

In the same manner as in Reference Example 2, there were obtained the following compounds:

1-(5-Bromo-2-pyrimidinyl)piperazine, M.P., 70°–72° C.;
1-(5-Fluoro-2-pyrimidinyl)piperazine, M.P., 38.5°–40° C.;
1-(4-Methyl-2-pyrimidinyl)piperazine, IR $\nu_{max}^{film}$ (cm$^{-1}$): 3180, 1560;
1-(5-Benzyloxy-2-pyrimidinyl)piperazine, M.P., 95°–96° C.;
1-(4,6-Dimethyl-2-pyrimidinyl)piperazine, M.P., 85°–86° C.;
1-(4,6-Dimethoxy-2-pyrimidinyl)piperazine, M.P., 100°–103° C;
1-(2-Amino-4-methyl-6-pyrimidinyl)piperazine, M.P., 177°–178° C.;
1-(5-Chloro-2-pyridyl)piperazine, M.P., 59°–61° C.;
1-(3-Methoxy-2-pyridyl)piperazine, M.P., 50.5°–51.5° C.;
1-(3-Cyano-2-pyridyl)piperazine, M.P., 104°–106° C.

EXAMPLE 1

A mixture of N-(4-bromobutyl)bicyclo[2.2.1]heptane-2,3-di-exo-carboximide (1.8 g), 1-(5-fluoro-2-pyrimidinyl)piperazine (1.09 g), potassium carbonate (1.7 g) and N,N-dimethylformamide (20 ml) was stirred at 100° to 110° C. for 4 hours. After completion of the reaction, the resultant mixture was poured into water and extracted with ethyl acetate. The oily residue was purified by silica gel column chromatography to give N-[4-{4-(5-fluoro-2-pyrimi- dinyl)-1-piperazinyl}butyl]-bicyclo[2.2.1]heptane-2,3-di- exo-carboximide (Compound No. 1). M.P., 126°–129° C.

In the same manner as in Example 1, the compounds as shown in Table 3 were obtained.

TABLE 3

(CH$_2$)$_n$ ... N—(CH$_2$)$_4$—N\_\_\_/N—R  (I)

| Compound No. | R | n | exo or endo | M.P. (°C.) |
|---|---|---|---|---|
| 2 | pyrimidinyl-Br | 1 | exp | 112–114 |
| 3 | pyrimidinyl-F | 1 | endo | 239–240 (HCl) |
| 4 | pyrimidinyl-F | 2 | — | 244 (dec.) (HCl) |
| 5 | pyrimidinyl-CH$_3$ | 1 | exo | 103–104 |
| 6 | pyrimidinyl-(CH$_3$)$_2$ | 1 | exo | 248–250 (HCl) |

TABLE 3-continued

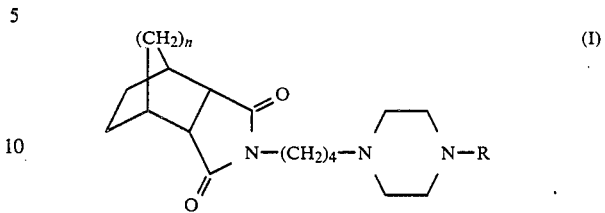

| Compound No. | R | n | exo or endo | M.P. (°C.) |
|---|---|---|---|---|
| 7 | 4,6-dimethoxy-2-pyrimidinyl (OCH₃, OCH₃) | 1 | exo | 105–107 |
| 8 | 4-methyl-6-amino-2-pyrimidinyl (CH₃, NH₂) | 1 | exo | 189–191 |
| 9 | 3-chloro-2-pyridyl (Cl) | 1 | exo | 196–200 (HCl) |
| 10 | 5-chloro-2-pyridyl (Cl) | 1 | exo | 121–122 |
| 11 | 3-methoxy-2-pyridyl (CH₃O) | 1 | exo | 196.5–198.5 (HCl) |
| 12 | 3-cyano-2-pyridyl (NC) | 1 | exo | 180–184 (HCl) |
| 13 | 5-benzyloxy-2-pyrimidinyl (OCH₂Ph) | 1 | exo | 116–119 |

EXAMPLE 2

A mixture of N-[4-{4-(5-benzyloxy-2-pyrimidinyl)1-piperazinyl}butyl]bicyclo[2.2.1]heptane-2,3-di-exo-carboximide (110 mg), 10 % palladium-carbon (11 mg) and methanol (30 ml) was hydrogenated at 100° C. under a pressure of 8 kg/cm² for 2 hours. After completion of the reaction, the palladium catalyst was removed by filtration. The filtrate was evaporated under reduced pressure, and the residue was purified by silica gel column chromatography using 10 % methanol in chloroform as an eluent to give N-[4-{4-(5-hydroxy-2-pyrimidinyl)-1-piperazinyl}butyl]bicyclo[2.2.1]heptane-2,3-di-exo-carboximide (Compound No. 14). M.P., 202°–203° C.

What is claimed is:

1. A succinimide derivative of the formula:

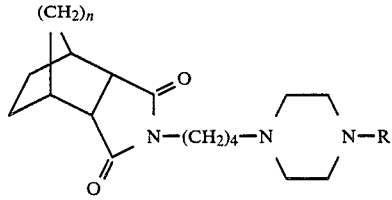

wherein R is a pyridyl or pyrimidinyl group substituted with at least one member selected from the group consisting of halogen, lower alkyl, lower alkoxy, cyano and hydroxyl, and n is an integer of 1 or 2, or a pharmaceutically acceptable acid addition salt thereof.

2. The succinimide derivative according to claim 1, wherein R is pyridyl.
3. The succinimide derivative according to claim 1, wherein R is pyrimidinyl.
4. The succinimide derivative according to claim 1, wherein n is 1.
5. The succinimide derivative according to claim 1, wherein n is 2.
6. The succinimide derivative according to claim 1, wherein the halogen is selected from the group consisting of fluorine, chlorine, bromine, and iodine.
7. The succinimide derivative according to claim 1, wherein the lower alkyl is selected from the group consisting of methyl, ethyl, n-propyl, isopropyl, n-butyl, and isobutyl.
8. The succinimide derivative according to claim 1, wherein the lower alkoxy is selected from the group consisting of methoxy, ethoxy, n-propoxy, isopropoxy, n-butoxy, and isobutoxy.
9. The succinimide derivative according to claim 3, wherein R is 5-halo-2-pyrimidinyl.
10. The succinimide derivative according to claim 9, wherein R is 5-fluoro-2-pyrimidinyl.
11. The succinimide derivative according to claim 3, wherein R is 5-bromo-2-pyrimidinyl.
12. The succinimide derivative according to claim 3, wherein R is 4-lower alkyl-2-pyrimidinyl.
13. The succinimide derivative according to claim 3, wherein R is 4,6-di(lower)alkyl-2-pyrimidinyl.
14. The succinimide derivative according to claim 3, wherein R is 4,6-di(lower)alkoxy-2-pyrimidinyl.
15. The succinimide derivative according to claim 2, wherein R is 3-halo-2-pyridyl.
16. The succinimide derivative according to claim 2, wherein R is 5-halo-2-pyridyl.
17. The succinimide derivative according to claim 2, wherein R is 3-lower alkoxy-2-pyridyl.
18. The succinimide derivative according to claim 2, wherein R is 3-cyano-2-pyridyl.
19. The succinimide derivative according to claim 3, wherein R is 5-hydroxy-2-pyrimidinyl.
20. A pharmaceutical composition for the treatment of anxiety which comprises as an active ingredient a pharmaceutically effective amount of at least one succinimide derivative (I) or its pharmaceutically acceptable acid addition salt as claimed in claim 1 and at least one pharmaceutically acceptable carrier or diluent.
21. A method for the treatment of anxiety which comprises administering a pharmaceutically effective amount of at least one succinimide derivative (I) or its pharmaceutically acceptable acid addition salt as claimed in claim 1 to a patient suffering from anxiety.

* * * * *